United States Patent
Cimen et al.

(10) Patent No.: US 12,100,502 B2
(45) Date of Patent: Sep. 24, 2024

(54) MULTI-VIEW MATCHING ACROSS CORONARY ANGIOGRAM IMAGES

(71) Applicant: SIEMENS HEALTHINEERS AG, Forchheim (DE)

(72) Inventors: Serkan Cimen, West Orange, NJ (US); Mehmet Akif Gulsun, Princeton, NJ (US); Puneet Sharma, Princeton Junction, NJ (US)

(73) Assignee: Siemens Healthineers AG, Forchheim (DE)

( * ) Notice: Subject to any disclaimer, the term of this patent is extended or adjusted under 35 U.S.C. 154(b) by 350 days.

(21) Appl. No.: 17/655,089

(22) Filed: Mar. 16, 2022

(65) Prior Publication Data
US 2023/0298736 A1 Sep. 21, 2023

(51) Int. Cl.
*G16H 30/40* (2018.01)
*G06T 7/00* (2017.01)
*G06V 10/82* (2022.01)

(52) U.S. Cl.
CPC ........... *G16H 30/40* (2018.01); *G06T 7/0016* (2013.01); *G06V 10/82* (2022.01); *G06T 2207/30048* (2013.01); *G06T 2207/30104* (2013.01)

(58) Field of Classification Search
CPC .................. G16H 30/40; G06T 7/0016; G06T 2207/30048; G06T 2207/30104; G06V 10/82; G06V 10/25; G06V 2201/03
USPC .......................................................... 382/128
See application file for complete search history.

(56) References Cited

U.S. PATENT DOCUMENTS

| | | | |
|---|---|---|---|
| 11,164,308 B2 * | 11/2021 | Wang | G06V 10/751 |
| 2016/0239963 A1 * | 8/2016 | Kariv | A61B 6/481 |
| 2018/0144466 A1 * | 5/2018 | Hsieh | G06T 7/0012 |
| 2021/0158580 A1 | 5/2021 | Barroyer et al. | |

OTHER PUBLICATIONS

Extended European Search Report (EESR) mailed Jul. 10, 2023 in corresponding European Patent Application No. 23162051.9.
Xiong, et al: "Landmark Detection and Tracking in Ultrasound using a CNN-RNN Framework", Dec. 2016 (Dec. 2016), pp. 1-6; Retrieved from the Internet: URL:https://www.researchgate.net/publication/316441246.

(Continued)

*Primary Examiner* — Juan A Torres

(57) ABSTRACT

Systems and methods for determining corresponding locations of points of interest in a plurality of input medical images are provided. A plurality of input medical images comprising a first input medical image and one or more additional input medical images is received. The first input medical image identifies a location of a point of interest. A set of features is extracted from each of the plurality of input medical images. Features between each of the sets of features are related using a machine learning based relational network. A location of the point of interest in each of the one or more additional input medical images that corresponds to the location of the point of interest in the first input medical image is identified based on the related features. The location of the point of interest in each of the one or more additional input medical images is output.

20 Claims, 8 Drawing Sheets

(56) References Cited

OTHER PUBLICATIONS

Belikova, et al: "Deep Learning for Spatio-Temporal Localization of Temporomandibular Joint in Ultrasound Videos", 2021 IEEE International Conference on Bioinformatics and Biomedicine (BIBM), IEEE, Dec. 9, 2021 (Dec. 9, 2021), pp. 1257-1261; DOI: 10.1109/BIBM52615.2021.9669857.
Lin, et al: "Cycle Ynet: Semi-supervised Tracking of 3D Anatomical Landmarks", 2020, 16th European Conference—Computer Vision—ECCV 2020, pp. 593-602.
Meinhardt, et al: "TrackFormer: Multi-Object Tracking with Transformers", 2022 IEEE/CVF Conference on Computer Vision and Pattern Recognition (CVPR), Apr. 28, 2021 (Apr. 28, 2021), pp. 8834-8844; 10.1109/CVPR52688.2022.00864, ISBN: 978—DOI: 1-6654-6946-3, Retrieved from the Internet: URL:https://arxiv.org/pdf/2101.02702v2.pdf.
Sarlin et al., "Superglue: Learning feature matching with graph neural networks", In Proceedings of the IEEE/CVF conference on computer vision and pattern recognition, 2019, pp. 1-9.
Xie et al., "CoTr: Efficiently Bridging CNN and Transformer for 3D Medical Image Segmentation", arXiv preprint arXiv:2103.03024, 2021, pp. 1-13.
Germain et al., "Visual Correspondence Hallucination", arXiv:2106.09711v3, 2022, pp. 1-28.

\* cited by examiner

Receive a plurality of input medical images comprising a first input medical image and one or more additional input medical images, the first input medical image identifying a location of a point of interest
102

Extract a set of features from each of the plurality of input medical images
104

Relate features between each of the sets of features using a machine learning based relational network
106

Identify, in each of the one or more additional input medical images, a location of the point of interest that corresponds to the location of the point of interest in the first input medical image based on the related features
108

Output the location of the point of interest in each of the one or more additional input medical images
110

MULTI-VIEW MATCHING ACROSS CORONARY ANGIOGRAM IMAGES

TECHNICAL FIELD

The present invention relates generally to multi-view matching of medical images, and in particular to multi-view matching across coronary angiogram images.

BACKGROUND

In PCI (percutaneous coronary intervention), multiple angiogram images of the coronary arteries of a patient are acquired by moving a C-arm to different positions around the patient. The angiogram images depict multiple views of the coronary arteries to provide additional information to clinicians for improved clinical decision making, resulting in better diagnosis and treatment. To exploit this multi-view information, whole or partial correspondences across images must be determined. However, determining correspondences between coronary angiogram images is challenging due to the complex structure of the coronary vessels, cardiac and respiratory motion, and patient and table motion.

BRIEF SUMMARY OF THE INVENTION

In accordance with one or more embodiments, systems and methods for determining corresponding locations of points of interest in a plurality of input medical images are provided. A plurality of input medical images comprising a first input medical image and one or more additional input medical images is received. The first input medical image identifies a location of a point of interest. A set of features is extracted from each of the plurality of input medical images. Features between each of the sets of features are related using a machine learning based relational network. A location of the point of interest in each of the one or more additional input medical images that corresponds to the location of the point of interest in the first input medical image is identified based on the related features. The location of the point of interest in each of the one or more additional input medical images is output.

In one embodiment, identifying the location of the point of interest in each of the one or more additional input medical images comprises generating a heatmap identifying the location of the point of interest for each of the one or more additional input medical images based on the related features using a convolutional neural network. In another embodiment, identifying the location of the point of interest in each of the one or more additional input medical images comprises determining coordinates identifying the location of the point of interest in each of the one or more additional input medical images using a multi-layer perceptron. In a further embodiment, identifying the location of the point of interest in each of the one or more additional input medical images comprises determining an assignment matrix identifying the location of the point of interest in each of the one or more additional input medical images using an optimal matching layer.

In one embodiment, one or more of the sets of features extracted from the plurality of input medical images are decoded to generate an additional output.

In one embodiment, x-ray geometry information used for acquiring the plurality of input medical images is received. The set of features is extracted from each of the plurality of input medical images and the x-ray geometry information.

In one embodiment, the location of the point of interest in the first input medical image is automatically determined using a machine learning based network. The location of the point of interest in the first input medical image is received from the machine learning based network. In another embodiment, user input is received from a user identifying the location of the point of interest in the first input medical image. wherein the point of interest comprises an anatomical landmark or an abnormality. The point of interest may comprise an anatomical landmark or an abnormality.

These and other advantages of the invention will be apparent to those of ordinary skill in the art by reference to the following detailed description and the accompanying drawings.

BRIEF DESCRIPTION OF THE DRAWINGS

FIG. 1 shows a method for determining corresponding locations of points of interest in a plurality of input medical images, in accordance with one or more embodiments;

DETAILED DESCRIPTION

The present invention generally relates to methods and systems for multi-view matching across coronary angiogram images. Embodiments of the present invention are described herein to give a visual understanding of such methods and systems. A digital image is often composed of digital representations of one or more objects (or shapes). The digital representation of an object is often described herein in terms of identifying and manipulating the objects. Such manipulations are virtual manipulations accomplished in the memory or other circuitry/hardware of a computer system. Accordingly, is to be understood that embodiments of the present invention may be performed within a computer system using data stored within the computer system.

Embodiments described herein provide for multi-view matching to automatically determine corresponding locations of points of interest across images of a coronary angiogram. Unlike conventional approaches, embodiments described herein provide for a fully automated approach for determining the corresponding locations of the points of interest using machine learning based networks that does not require input from a user.

Figure 2:
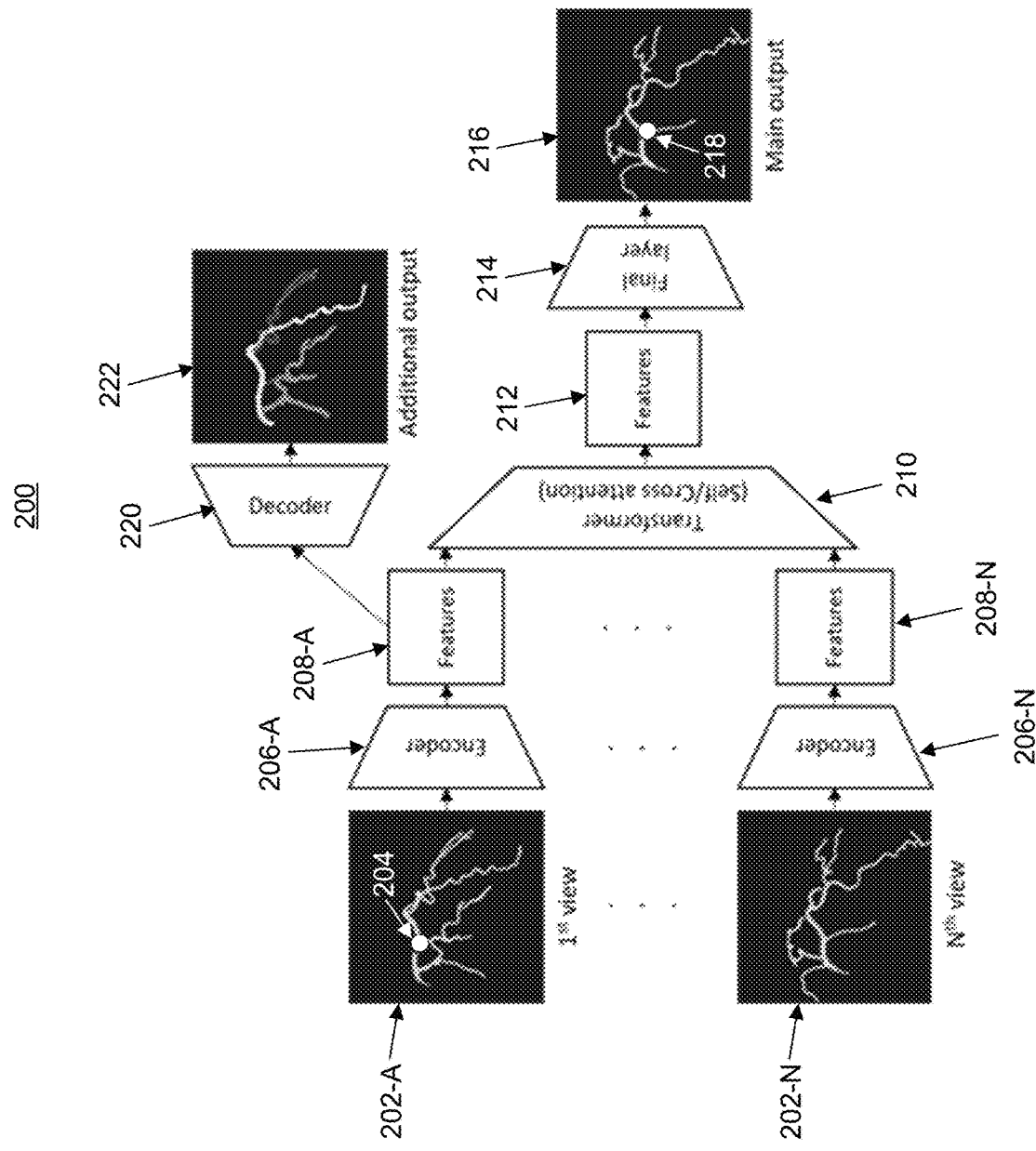
FIG. 2 shows a workflow for determining corresponding location of points of interest in a plurality of input medical images, in accordance with one or more embodiments.

FIG. 1 shows a method 100 for determining corresponding locations of points of interest in a plurality of input medical images, in accordance with one or more embodiments. The steps of method 100 may be performed by one or more suitable computing devices, such as, e.g., computer 802 of FIG. 8. FIG. 2 shows a workflow 200 for determining corresponding locations of points of interest in a plurality of input medical images, in accordance with one or more embodiments. FIG. 1 and FIG. 2 will be described together.

At step 102 of FIG. 1, a plurality of input medical images is received. The plurality of input medical images comprises a first input medical image and one or more additional input medical images. The first input medical image identifies a location of a point of interest. In one example, as shown in workflow 200 of FIG. 2, the plurality of input medical images comprises first input medical image 202-A, . . . , additional input medical image 202-N (collectively referred to as plurality of input medical images 202), where N is any integer greater than 1. First input medical image 202-A identifies a location 204 of a point of interest.

In one embodiment, each of the plurality of input medical images depicts coronary arteries of a patient. However, the plurality of input medical images may depict any other anatomical object of interest, such as, e.g., organs, bones, vessels, lesions, etc. of the patient. The plurality of input medical images may be a sequence of medical images depicting different views of the anatomical object of interest acquired at a particular time or may be a time series of medical images acquired over time (e.g., to monitor the progression of a disease or medical treatment). In one embodiment, the plurality of input medical images may also comprise images derived from a medical image, such as, e.g., a response map (e.g., a vesselness response map).

The location of the point of interest may be the location of any suitable point of interest in the first input medical image, such as, e.g., a location of an anatomical landmark or a location of an abnormality (e.g., a lesion or a nodule). The location of the point of interest in the first input medical image may be manually defined by a user (e.g., a clinician) or may be automatically defined. For example, the location of the point of interest in the first input medical image may be automatically defined as a location of a lesion automatically identified by a machine learning based lesion detection network.

In one embodiment, the plurality of input medical images are x-ray images, e.g., acquired during a coronary angiography. However, the plurality of input medical image may be of any other suitable modality, such as, e.g., MRI (magnetic resonance imaging), US (ultrasound), CT (computed tomography), or any other medical imaging modality or combinations of medical imaging modalities. Each of the plurality of input medical images may be of a same modality or two or more of the plurality of input medical images may be of different modalities. The plurality of input medical images may be 2D (two dimensional) images and/or 3D (three dimensional) volumes. Accordingly, reference herein to a pixel of an image equally refers to a voxel of a volume. The plurality of input medical images may be received directly from an image acquisition device, such as, e.g., a X-ray scanner, as the medical images are acquired, may be received by loading previously acquired medical images from a storage or memory of a computer system, and/or may be received from a remote computer system.

At step 104 of FIG. 1, a set of features is extracted from each of the plurality of input medical images. The set of features may be extracted from each of the plurality of input medical images using any suitable approach. In one embodiment, the set of features is extracted from each of the plurality of input medical images using a machine learning based network, such as, e.g., an encoder neural network. For example, as shown in workflow 200 of FIG. 2, encoder networks 206-A, . . . , 206-N (collectively referred to as encoder networks 206) respectively extract a set of features 208-A, . . . , 208-N (collectively referred to as sets of features 208) from each input medical image 202-A, . . . , 202-N. While encoder networks 206 are separately shown in workflow 200, it should be understood that encoder networks 206 is the same encoder network separately applied to each of the plurality of input medical images 202 to respectively extract sets of features 208. Encoders 206 respectively receive input medical images 202 as input and generate sets of features 208 as output. The features of the sets of features 208 may be low-level, latent features of the plurality of input medical images 202 representing the most important features of the plurality of input medical images 202.

At step 106 of FIG. 1, features between each of the sets of features are related using a machine learning based relational network. The features may be related using any suitable machine learning based network, such as, e.g., a transformer neural network. For example, as shown in workflow 200 of FIG. 2, transformer network 210 relates features within and across sets of features 208 to generate related features 212. Transformer network 210 may be implemented with self attention or cross attention. Transformer network 210 receives sets of features 208 as input and generates related features 212 as output. The sets of features 208 may be combined (e.g., concatenated with positional encodings) before being input to transformer network 210. Transformer network 210 matches features in one input medical image 202 to the other input medical images 202. For example, transformer network 210 may relate each pixel in one input medical image 202 to the other input medical images 202.

Figure 3:
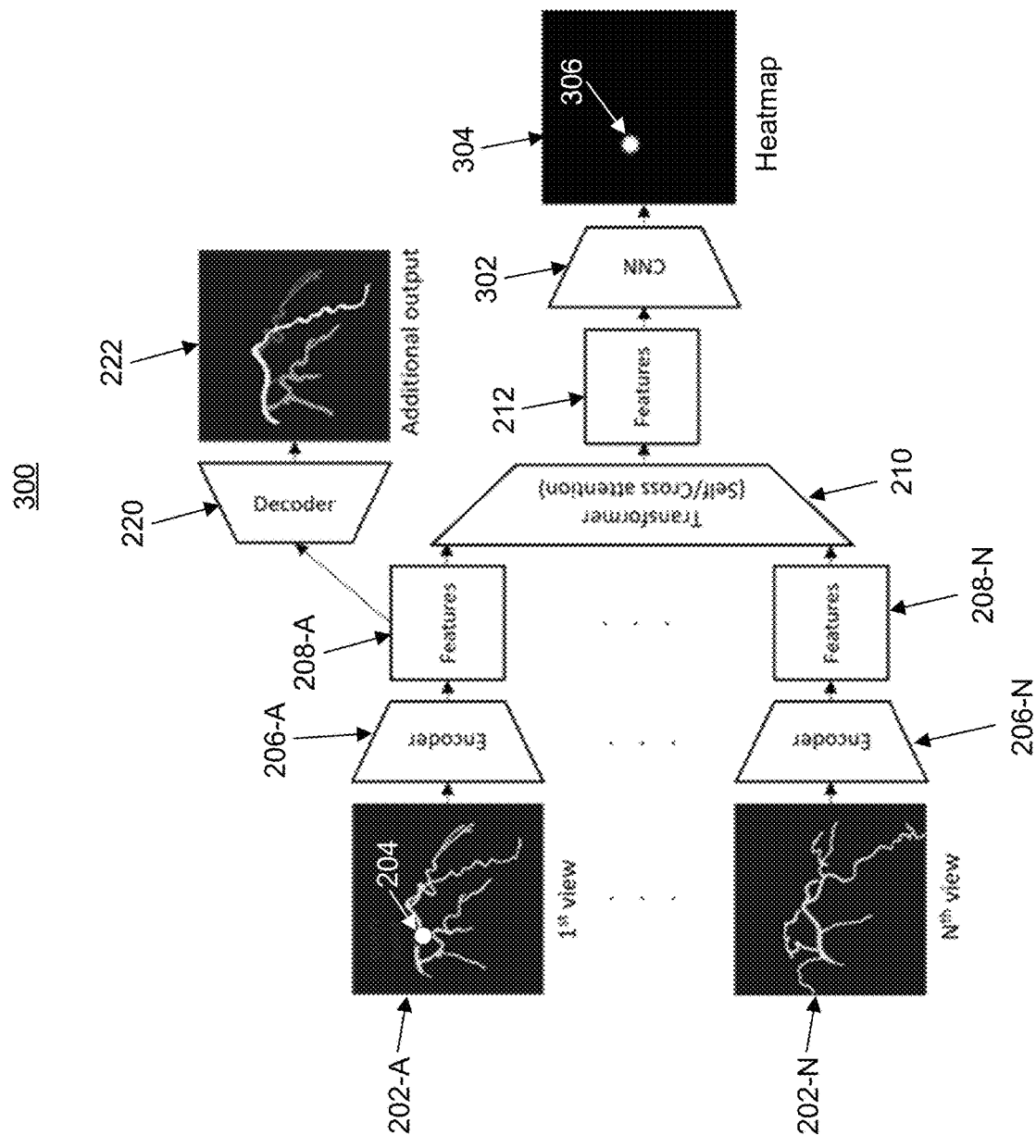
FIG. 3 shows a workflow for determining corresponding points of interest in a plurality of input medical images using a CNN (convolutional neural network) as the final layer, in accordance with one or more embodiments.
Figure 4:
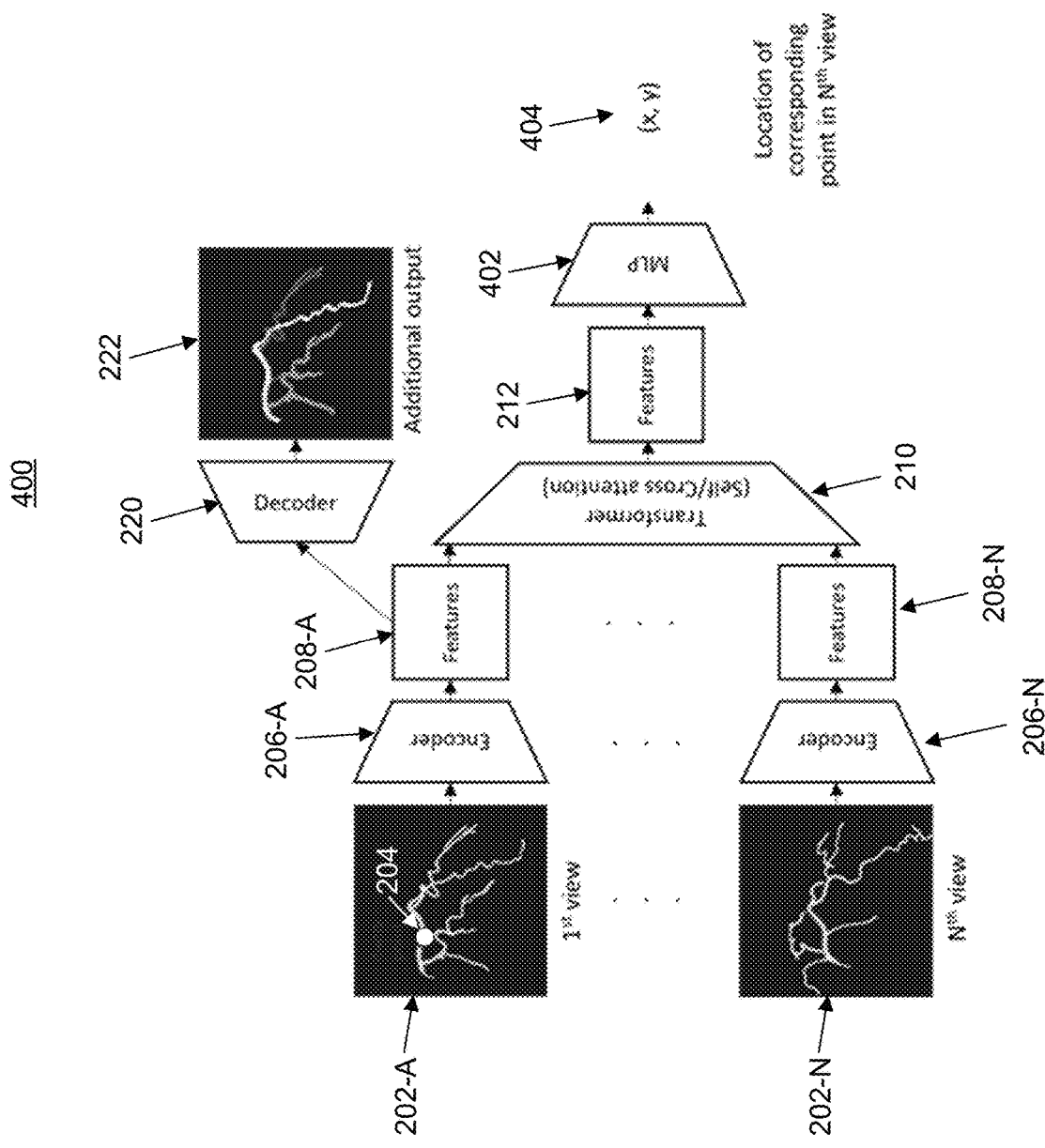
FIG. 4 shows a workflow for determining corresponding points of interest in a plurality of input medical images using an MLP (multi-layer perceptron) as the final layer, in accordance with one or more embodiments.
Figure 5:
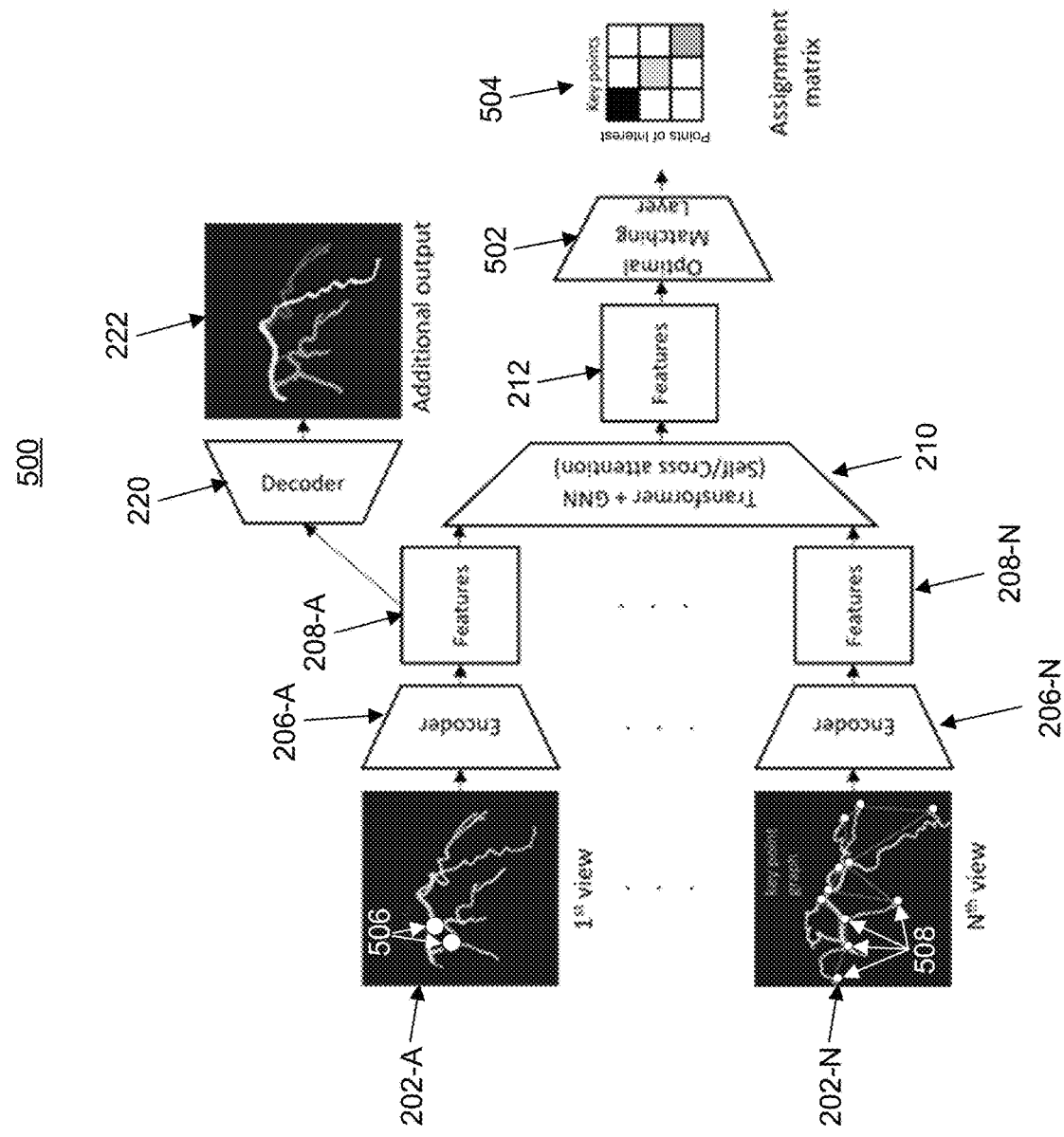
FIG. 5 shows a workflow for determining corresponding points of interest in a plurality of input medical images using an optimal matching layer as the final layer, in accordance with one or more embodiments

At step 108 of FIG. 1, a location of the point of interest in each of the one or more additional input medical images that corresponds to the location of the point of interest in the first input medical image is identified based on the related features. The locations of the point of interest in the first input medical image and the one or more additional input medical images correspond when such locations depict the patient (or any other object of interest) at a same position in a given patient coordinate system of the patient or depict the same anatomical location on an object of interest (such as, e.g., organ). In one embodiment, the location of the point of interest in each of the one or more additional input medical images is identified by a machine learning based network. For example, as shown in FIG. 2, a final layer 214 generates output image 216 identifying a location 218 of the point of interest based on related features 212. Output image 216 may be a reproduction or recreation of additional input medical image 202-N having the location 218 of the point of interest overlaid thereon. Final layer 214 may generate an output image 216 for each of the one or more additional input medical images. Final layer 214 may be any suitable machine learning based network for identifying the location of the point of interest in each of the one or more additional input medical images. FIGS. 3-5 shows various embodiments of workflow 200 of FIG. 2 using different machine learning based networks for final layer 214, where like reference numbers represent the same or similar elements.

FIG. 3 shows a workflow 300 for determining corresponding points of interest in a plurality of input medical images using a CNN (convolutional neural network) as the final layer, in accordance with one or more embodiments. Workflow 300 of FIG. 3 shows an embodiment of workflow 200 of FIG. 2 where final layer 214 is CNN 302. CNN 302 receives related features 212 as input and generates heatmap 304 identifying location 306 of a point of interest as output. Heatmap 304 is a pixelwise (or voxelwise) probability map having pixels corresponding to the additional input medical image 202-N. Each respective pixel of the probability map has an intensity value ranging from, e.g., 0 to 1 representing a probability that the respective pixel corresponds to the location 204 of the point of interest in the first input medical image 202-A. Heatmap 304 may be represented as a pixelwise binary map by applying a threshold (e.g., 0.5) to each pixel intensity value in the probability map. Each respective pixel of the binary map has an intensity value of, e.g., 1 indicating that the respective pixel corresponds to the location 204 of the point of interest in the first input medical image 202-A or an intensity value of, e.g., 0 indicating that the respective pixel does not correspond to the location 204 of the point of interest in the first input medical image 202-A. A heatmap may be generated identifying a location of the point of interest for each additional input medical image.

FIG. 4 shows a workflow 400 for determining corresponding points of interest in a plurality of input medical images using an MLP (multi-layer perceptron) as the final layer, in accordance with one or more embodiments. Workflow 300 of FIG. 3 shows an embodiment of workflow 200 of FIG. 2 where final layer 214 is MLP 402. MLP 402 formulates the problem as an implicit function learning. MLP 402 receives related features 212 as input and generates (x, y) coordinates 404 as output. Coordinates 404 identify the location of the point of interest, that corresponds to location 204 of the point of interest in the first input medical image 202-A, in each of the additional input medical image 202-N. Coordinates may be generated identifying the location of the point of interest for each additional input medical image.

FIG. 5 shows a workflow 500 for determining corresponding points of interest in a plurality of input medical images using an optimal matching layer as the final layer, in accordance with one or more embodiments. Workflow 300 of FIG. 3 shows an embodiment of workflow 200 of FIG. 2 where final layer 214 is optimal matching layer 502. In workflow 500, first input medical image 202-A comprises two locations 506 of points of interest and each additional input medical image 202-N comprises locations 508 of a plurality of key points. The points of interest and the key points can be used to build a graph with extracted features and a GNN (graph neural network) with self or cross attention modules can be used to estimate the correspondences between the points of interest and the key points. Optimal matching layer 502 receives related features 212 as input and generates an assignment matrix 504 as output. Assignment matrix 504 defines the correspondences between the locations 506 points of interest and the locations 508 of the key points. Optimal matching layer 502 may be, for example, iterations of a differentiable Sinkhorn algorithm (with scores computed using the inner product of feature vectors of key/query points after attention layers).

At step 110 of FIG. 1, the location of the point of interest in each of the one or more additional input medical images is output. For example, the location of the point of interest in each of the one or more additional input medical images can be output by displaying the location on a display device of a computer system, storing the location on a memory or storage of a computer system, or by transmitting the location to a remote computer system.

In one embodiment, the location of the point of interest in each of the one or more additional input medical images may be post-processed based on additional information, such as, e.g., the distance to epipolar lines, the segment labels of a target coronary branch, geometric features of the target coronary branch (e.g., scale, distance to proximal point), etc.

In one embodiment, the location of the point of interest in each of the one or more additional input medical images may be input to a system for performing further medical imaging analysis tasks, such as, e.g., vessel labeling, stenosis detection, bifurcation detection, centerline extraction, etc. In another embodiment, corresponding locations of the point of interest in the plurality of input medical images may be used to detect technical issues with the image acquisition, such as, e.g., detection of table panning, motion, etc.

In one embodiment, a decoder may be applied to decode one or more of the sets of features extracted from each of the plurality of input medical images to generate additional outputs. For example, as shown in FIG. 2, decoder 220 may be applied to decode the set of features 208-A to generate additional output 222. The additional output 222 may help in training the machine learning framework to better regularize learning. The additional output 222 may be, for example, branch labels, depth maps, 3D reconstruction, etc.).

In one embodiment, where the plurality of input medical images 202 comprises x-ray images, encodings based on x-ray geometry information used for acquiring the x-ray images may be fed as input into encoders 206 and/or transformer network 210.

In one embodiment, where the plurality of input medical images 202 comprises x-ray images, x-ray geometry may be used as prior information fed as input into one or more of the machine learning based networks in workflow 200. This may be useful for bi-plane systems where the plurality of input medical images 202 comprise a plurality of simultaneous images of the same anatomical object of interest (with no additional patient or table motion across views). For example, epipolar lines may be used to define positional encodings for the transformer network 210.

In one embodiment, workflow 200 may take into account global image features, which may resolve geometric ambiguities by, e.g., learning anatomical context (e.g., vessel direction, upstream/downstream, etc.).

In one embodiment, the machine learning based framework, including encoder networks 206, transformer network 210, final layer 214, and decoder 220, for implementing workflow 200 may be trained using synthetic or real images (e.g., coronary angiography images) or images derived therefrom. To generate synthetic images, a set of CTA (coronary CT angiography) images may be annotated and a set of synthetic images may be generated from the annotated set of CTA images using generative neural networks or generative derived images such as, e.g., vesselness response maps. Manually annotating correspondences for all locations across the real CTA images may be difficult. In one embodiment, salient points or regions (e.g., catheter tip, bifurcations, lesions, etc.) may be annotated and matched across angiography images to generate training data.

Embodiments described herein are described with respect to the claimed systems as well as with respect to the claimed methods. Features, advantages or alternative embodiments herein can be assigned to the other claimed objects and vice versa. In other words, claims for the systems can be improved with features described or claimed in the context of the methods. In this case, the functional features of the method are embodied by objective units of the providing system.

Furthermore, certain embodiments described herein are described with respect to methods and systems utilizing trained machine learning based networks (or models), as well as with respect to methods and systems for training machine learning based networks. Features, advantages or alternative embodiments herein can be assigned to the other claimed objects and vice versa. In other words, claims for methods and systems for training a machine learning based network can be improved with features described or claimed in context of the methods and systems for utilizing a trained machine learning based network, and vice versa.

In particular, the trained machine learning based networks applied in embodiments described herein can be adapted by the methods and systems for training the machine learning based networks. Furthermore, the input data of the trained machine learning based network can comprise advantageous features and embodiments of the training input data, and vice versa. Furthermore, the output data of the trained machine learning based network can comprise advantageous features and embodiments of the output training data, and vice versa.

In general, a trained machine learning based network mimics cognitive functions that humans associate with other human minds. In particular, by training based on training data, the trained machine learning based network is able to adapt to new circumstances and to detect and extrapolate patterns.

In general, parameters of a machine learning based network can be adapted by means of training. In particular, supervised training, semi-supervised training, unsupervised training, reinforcement learning and/or active learning can be used. Furthermore, representation learning (an alternative term is "feature learning") can be used. In particular, the parameters of the trained machine learning based network can be adapted iteratively by several steps of training.

In particular, a trained machine learning based network can comprise a neural network, a support vector machine, a decision tree, and/or a Bayesian network, and/or the trained machine learning based network can be based on k-means clustering, Q-learning, genetic algorithms, and/or association rules. In particular, a neural network can be a deep neural network, a convolutional neural network, or a convolutional deep neural network. Furthermore, a neural network can be an adversarial network, a deep adversarial network and/or a generative adversarial network.

Figure 6:
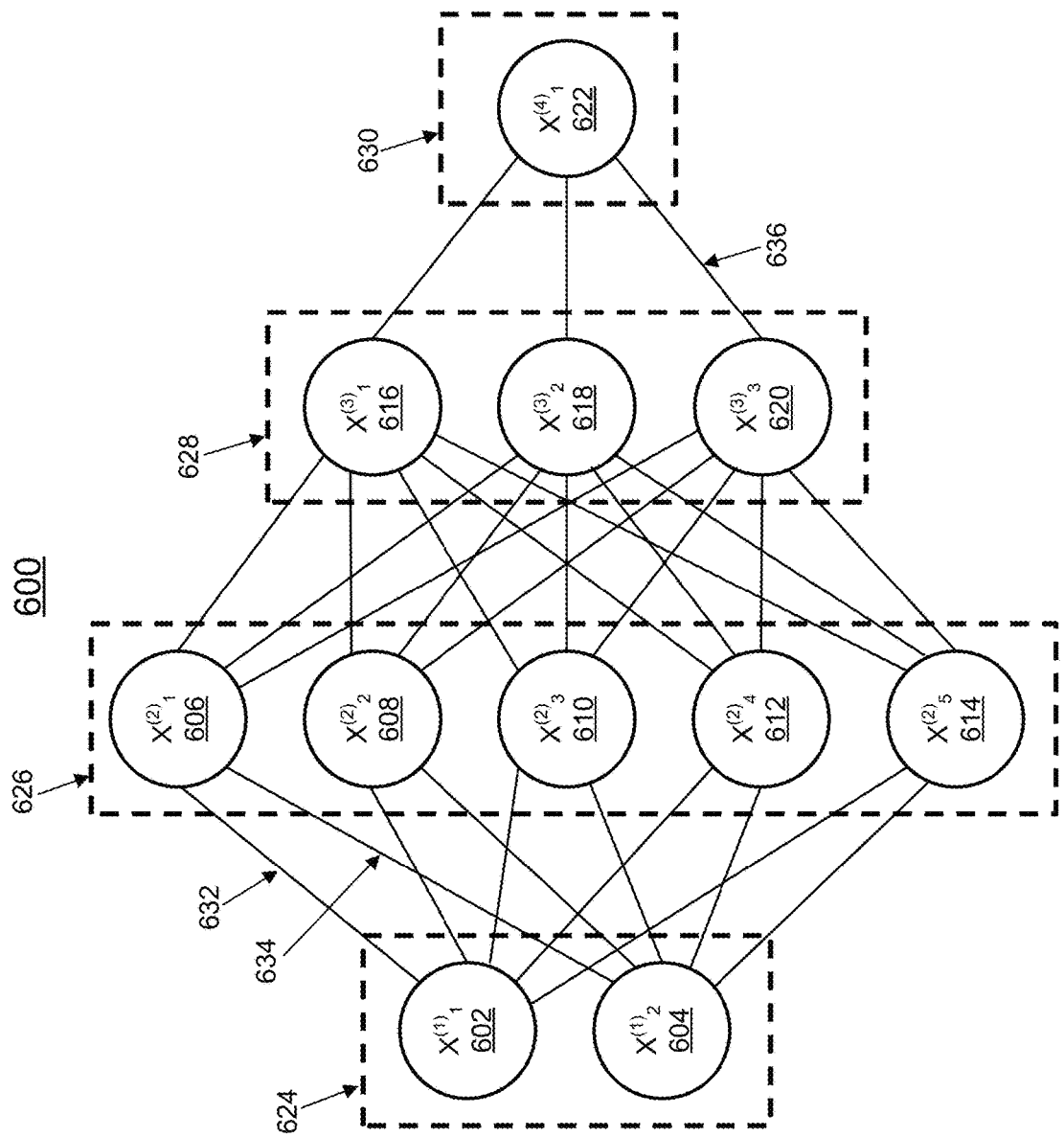
FIG. 6 shows an exemplary artificial neural network that may be used to implement one or more embodiments.

FIG. 6 shows an embodiment of an artificial neural network 600, in accordance with one or more embodiments. Alternative terms for "artificial neural network" are "neural network", "artificial neural net" or "neural net". Machine learning networks described herein, such as, e.g., the encoder network utilized at step 104, the relational network utilized at step 106, and the machine learning based network utilized at step 108 of FIG. 1, the encoders 206, the transformer network 210, and the final layer 214, and the decoder 220 of FIG. 2, CNN 302 of FIG. 3, MLP 402 of FIG. 4, and optimal matching layer 502 of FIG. 5, may be implemented using artificial neural network 600.

The artificial neural network 600 comprises nodes 602-622 and edges 632, 634, ..., 636, wherein each edge 632, 634, ..., 636 is a directed connection from a first node 602-622 to a second node 602-622. In general, the first node 602-622 and the second node 602-622 are different nodes 602-622, it is also possible that the first node 602-622 and the second node 602-622 are identical. For example, in FIG. 6, the edge 632 is a directed connection from the node 602 to the node 606, and the edge 634 is a directed connection from the node 604 to the node 606. An edge 632, 634, ..., 636 from a first node 602-622 to a second node 602-622 is also denoted as "ingoing edge" for the second node 602-622 and as "outgoing edge" for the first node 602-622.

In this embodiment, the nodes 602-622 of the artificial neural network 600 can be arranged in layers 624-630, wherein the layers can comprise an intrinsic order introduced by the edges 632, 634, ..., 636 between the nodes 602-622. In particular, edges 632, 634, ..., 636 can exist only between neighboring layers of nodes. In the embodiment shown in FIG. 6, there is an input layer 624 comprising only nodes 602 and 604 without an incoming edge, an output layer 630 comprising only node 622 without outgoing edges, and hidden layers 626, 628 in-between the input layer 624 and the output layer 630. In general, the number of hidden layers 626, 628 can be chosen arbitrarily. The number of nodes 602 and 604 within the input layer 624 usually relates to the number of input values of the neural network 600, and the number of nodes 622 within the output layer 630 usually relates to the number of output values of the neural network 600.

In particular, a (real) number can be assigned as a value to every node 602-622 of the neural network 600. Here, $x^{(n)}_i$ denotes the value of the i-th node 602-622 of the n-th layer 624-630. The values of the nodes 602-622 of the input layer 624 are equivalent to the input values of the neural network 600, the value of the node 622 of the output layer 630 is equivalent to the output value of the neural network 600. Furthermore, each edge 632, 634, ..., 636 can comprise a weight being a real number. Here, $w^{(m,n)}_{i,j}$ denotes the weight of the edge between the i-th node 602-622 of the m-th layer 624-630 and the j-th node 602-622 of the n-th layer 624-630. Furthermore, the abbreviation $w^{(n)}_{i,j}$ is defined for the weight $w^{(n,n+1)}_{i,j}$.

In particular, to calculate the output values of the neural network 600, the input values are propagated through the neural network. In particular, the values of the nodes 602-622 of the (n+1)-th layer 624-630 can be calculated based on the values of the nodes 602-622 of the n-th layer 624-630 by $$z^{(n+1)}_j = f(\Sigma_i x_i^{(n)} \cdot w_{i,j}^{(n)}).$$

Herein, the function f is a transfer function (another term is "activation function"). Known transfer functions are step functions, sigmoid function (e.g. the logistic function, the generalized logistic function, the hyperbolic tangent, the Arctangent function, the error function, the smoothstep function) or rectifier functions. The transfer function is mainly used for normalization purposes.

In particular, the values are propagated layer-wise through the neural network, wherein values of the input layer 624 are given by the input of the neural network 600, wherein values of the first hidden layer 626 can be calculated based on the values of the input layer 624 of the neural network, wherein values of the second hidden layer 628 can be calculated based in the values of the first hidden layer 626, etc.

In order to set the values $w^{(m,n)}_{i,j}$ for the edges, the neural network 600 has to be trained using training data. In particular, training data comprises training input data and training output data (denoted as $t_i$). For a training step, the neural network 600 is applied to the training input data to generate calculated output data. In particular, the training data and the calculated output data comprise a number of values, said number being equal with the number of nodes of the output layer.

In particular, a comparison between the calculated output data and the training data is used to recursively adapt the weights within the neural network 600 (backpropagation algorithm). In particular, the weights are changed according to $$w_{i,j}^{(n)} = w_{i,j}^{(n)} - \gamma \cdot \delta_j^{(n)} \cdot x_i^{(n)}$$

wherein γ is a learning rate, and the numbers $\delta^{(n)}_j$ can be recursively calculated as $$\delta_j^{(n)} = (\Sigma_k \delta_k^{(n+1)} \cdot w_{j,k}^{(n+1)}) \cdot f'(\Sigma_i x_i^{(n)} \cdot w_{i,j}^{(n)})$$

based on $\delta^{(n+1)}_j$, if the (n+1)-th layer is not the output layer, and $$\delta_j^{(n)} = (x_k^{(n+1)} - t_j^{(n+1)}) \cdot f'(\Sigma_i x_i^{(n)} \cdot w_{i,j}^{(n)})$$

if the (n+1)-th layer is the output layer 630, wherein f' is the first derivative of the activation function, and $y^{(n+1)}_j$ is the comparison training value for the j-th node of the output layer 630.

Figure 7:
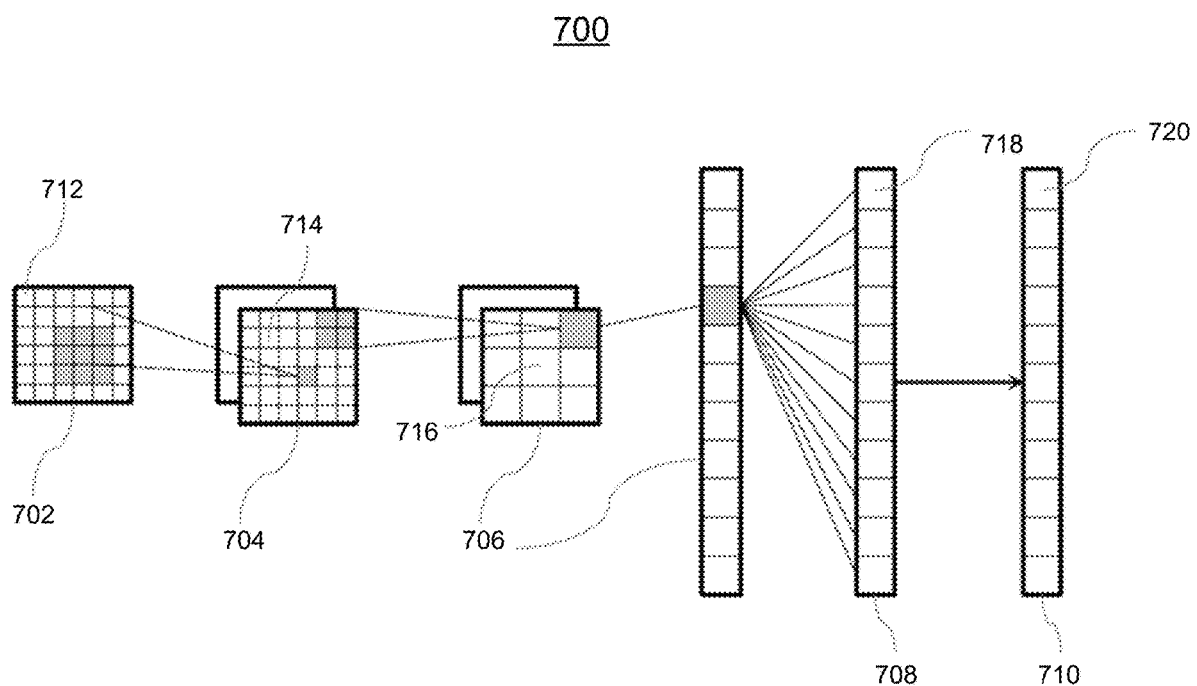
FIG. 7 shows a convolutional neural network that may be used to implement one or more embodiments.

FIG. 7 shows a convolutional neural network 700, in accordance with one or more embodiments. Machine learning networks described herein, such as, e.g., the encoder network utilized at step 104, the relational network utilized at step 106, and the machine learning based network utilized at step 108 of FIG. 1, the encoders 206, the transformer network 210, and the final layer 214, and the decoder 220 of FIG. 2, CNN 302 of FIG. 3, MLP 402 of FIG. 4, and optimal matching layer 502 of FIG. 5, may be implemented using convolutional neural network 700.

In the embodiment shown in FIG. 7, the convolutional neural network comprises 700 an input layer 702, a convolutional layer 704, a pooling layer 706, a fully connected layer 708, and an output layer 710. Alternatively, the convolutional neural network 700 can comprise several convolutional layers 704, several pooling layers 706, and several fully connected layers 708, as well as other types of layers. The order of the layers can be chosen arbitrarily, usually fully connected layers 708 are used as the last layers before the output layer 710.

In particular, within a convolutional neural network 700, the nodes 712-720 of one layer 702-710 can be considered to be arranged as a d-dimensional matrix or as a d-dimensional image. In particular, in the two-dimensional case the value of the node 712-720 indexed with i and j in the n-th layer 702-710 can be denoted as $x^{(n)}_{[i,j]}$. However, the arrangement of the nodes 712-720 of one layer 702-710 does not have an effect on the calculations executed within the convolutional neural network 700 as such, since these are given solely by the structure and the weights of the edges.

In particular, a convolutional layer 704 is characterized by the structure and the weights of the incoming edges forming a convolution operation based on a certain number of kernels. In particular, the structure and the weights of the incoming edges are chosen such that the values $x^{(n)}_k$ of the nodes 714 of the convolutional layer 704 are calculated as a convolution $x^{(n)}_k = K_k * x^{(n-1)}$ based on the values $x^{(n-1)}$ of the nodes 712 of the preceding layer 702, where the convolution * is defined in the two-dimensional case as $$x_k^{(n)}[i,j] = (K_k * x^{(n-1)})[i,j] = \Sigma_i \Sigma_j K_k[i',j'] \cdot x^{(n-1)}[i-i',j-j'].$$

Here the k-th kernel $K_k$ is a d-dimensional matrix (in this embodiment a two-dimensional matrix), which is usually small compared to the number of nodes 712-718 (e.g. a 3×3 matrix, or a 5×5 matrix). In particular, this implies that the weights of the incoming edges are not independent, but chosen such that they produce said convolution equation. In particular, for a kernel being a 3×3 matrix, there are only 9 independent weights (each entry of the kernel matrix corresponding to one independent weight), irrespectively of the number of nodes 712-720 in the respective layer 702-710. In particular, for a convolutional layer 704, the number of nodes 714 in the convolutional layer is equivalent to the number of nodes 712 in the preceding layer 702 multiplied with the number of kernels.

If the nodes 712 of the preceding layer 702 are arranged as a d-dimensional matrix, using a plurality of kernels can be interpreted as adding a further dimension (denoted as "depth" dimension), so that the nodes 714 of the convolutional layer 704 are arranged as a (d+1)-dimensional matrix. If the nodes 712 of the preceding layer 702 are already arranged as a (d+1)-dimensional matrix comprising a depth dimension, using a plurality of kernels can be interpreted as expanding along the depth dimension, so that the nodes 714 of the convolutional layer 704 are arranged also as a (d+1)-dimensional matrix, wherein the size of the (d+1)-dimensional matrix with respect to the depth dimension is by a factor of the number of kernels larger than in the preceding layer 702.

The advantage of using convolutional layers 704 is that spatially local correlation of the input data can exploited by enforcing a local connectivity pattern between nodes of adjacent layers, in particular by each node being connected to only a small region of the nodes of the preceding layer.

In embodiment shown in FIG. 7, the input layer 702 comprises 36 nodes 712, arranged as a two-dimensional 6×6 matrix. The convolutional layer 704 comprises 72 nodes 714, arranged as two two-dimensional 6×6 matrices, each of the two matrices being the result of a convolution of the values of the input layer with a kernel. Equivalently, the nodes 714 of the convolutional layer 704 can be interpreted as arranges as a three-dimensional 6×6×2 matrix, wherein the last dimension is the depth dimension.

A pooling layer 706 can be characterized by the structure and the weights of the incoming edges and the activation function of its nodes 716 forming a pooling operation based on a non-linear pooling function f. For example, in the two dimensional case the values $x^{(n)}$ of the nodes 716 of the pooling layer 706 can be calculated based on the values $x^{(n-1)}$ of the nodes 714 of the preceding layer 704 as $$x^{(n)}[i,j] = f(x^{(n-1)}[id_1, jd_2], \ldots, x^{(n-1)}[id_1+d_1-1, jd_2+d_2-1])$$

In other words, by using a pooling layer 706, the number of nodes 714, 716 can be reduced, by replacing a number d1·d2 of neighboring nodes 714 in the preceding layer 704 with a single node 716 being calculated as a function of the values of said number of neighboring nodes in the pooling layer. In particular, the pooling function f can be the max-function, the average or the L2-Norm. In particular, for a pooling layer 706 the weights of the incoming edges are fixed and are not modified by training.

The advantage of using a pooling layer 706 is that the number of nodes 714, 716 and the number of parameters is reduced. This leads to the amount of computation in the network being reduced and to a control of overfitting.

In the embodiment shown in FIG. 7, the pooling layer 706 is a max-pooling, replacing four neighboring nodes with only one node, the value being the maximum of the values of the four neighboring nodes. The max-pooling is applied to each d-dimensional matrix of the previous layer; in this embodiment, the max-pooling is applied to each of the two two-dimensional matrices, reducing the number of nodes from 72 to 18.

A fully-connected layer 708 can be characterized by the fact that a majority, in particular, all edges between nodes 716 of the previous layer 706 and the nodes 718 of the fully-connected layer 708 are present, and wherein the weight of each of the edges can be adjusted individually.

In this embodiment, the nodes 716 of the preceding layer 706 of the fully-connected layer 708 are displayed both as two-dimensional matrices, and additionally as non-related nodes (indicated as a line of nodes, wherein the number of nodes was reduced for a better presentability). In this embodiment, the number of nodes 718 in the fully connected layer 708 is equal to the number of nodes 716 in the preceding layer 706. Alternatively, the number of nodes 716, 718 can differ.

Furthermore, in this embodiment, the values of the nodes 720 of the output layer 710 are determined by applying the Softmax function onto the values of the nodes 718 of the preceding layer 708. By applying the Softmax function, the sum the values of all nodes 720 of the output layer 710 is 1, and all values of all nodes 720 of the output layer are real numbers between 0 and 1.

A convolutional neural network 700 can also comprise a ReLU (rectified linear units) layer or activation layers with non-linear transfer functions. In particular, the number of nodes and the structure of the nodes contained in a ReLU layer is equivalent to the number of nodes and the structure of the nodes contained in the preceding layer. In particular, the value of each node in the ReLU layer is calculated by applying a rectifying function to the value of the corresponding node of the preceding layer.

The input and output of different convolutional neural network blocks can be wired using summation (residual/dense neural networks), element-wise multiplication (attention) or other differentiable operators. Therefore, the convolutional neural network architecture can be nested rather than being sequential if the whole pipeline is differentiable.

In particular, convolutional neural networks 700 can be trained based on the backpropagation algorithm. For preventing overfitting, methods of regularization can be used, e.g. dropout of nodes 712-720, stochastic pooling, use of artificial data, weight decay based on the L1 or the L2 norm, or max norm constraints. Different loss functions can be combined for training the same neural network to reflect the joint training objectives. A subset of the neural network parameters can be excluded from optimization to retain the weights pretrained on another datasets.

Systems, apparatuses, and methods described herein may be implemented using digital circuitry, or using one or more computers using well-known computer processors, memory units, storage devices, computer software, and other components. Typically, a computer includes a processor for executing instructions and one or more memories for storing instructions and data. A computer may also include, or be coupled to, one or more mass storage devices, such as one or more magnetic disks, internal hard disks and removable disks, magneto-optical disks, optical disks, etc.

Systems, apparatus, and methods described herein may be implemented using computers operating in a client-server relationship. Typically, in such a system, the client computers are located remotely from the server computer and interact via a network. The client-server relationship may be defined and controlled by computer programs running on the respective client and server computers.

Systems, apparatus, and methods described herein may be implemented within a network-based cloud computing system. In such a network-based cloud computing system, a server or another processor that is connected to a network communicates with one or more client computers via a network. A client computer may communicate with the server via a network browser application residing and operating on the client computer, for example. A client computer may store data on the server and access the data via the network. A client computer may transmit requests for data, or requests for online services, to the server via the network. The server may perform requested services and provide data to the client computer(s). The server may also transmit data adapted to cause a client computer to perform a specified function, e.g., to perform a calculation, to display specified data on a screen, etc. For example, the server may transmit a request adapted to cause a client computer to perform one or more of the steps or functions of the methods and workflows described herein, including one or more of the steps or functions of FIGS. 1-5. Certain steps or functions of the methods and workflows described herein, including one or more of the steps or functions of FIGS. 1-5, may be performed by a server or by another processor in a network-based cloud-computing system. Certain steps or functions of the methods and workflows described herein, including one or more of the steps of FIGS. 1-5, may be performed by a client computer in a network-based cloud computing system. The steps or functions of the methods and workflows described herein, including one or more of the steps of FIGS. 1-5, may be performed by a server and/or by a client computer in a network-based cloud computing system, in any combination.

Systems, apparatus, and methods described herein may be implemented using a computer program product tangibly embodied in an information carrier, e.g., in a non-transitory machine-readable storage device, for execution by a programmable processor; and the method and workflow steps described herein, including one or more of the steps or functions of FIGS. 1-5, may be implemented using one or more computer programs that are executable by such a processor. A computer program is a set of computer program instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Figure 8:
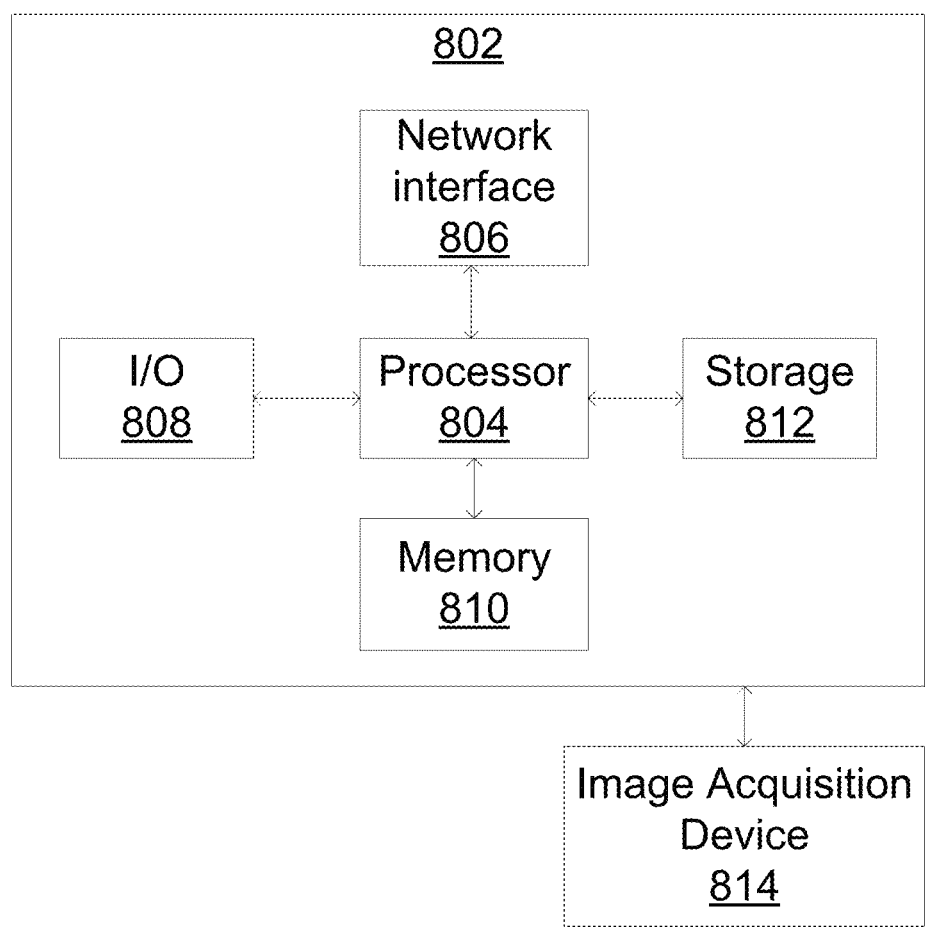
FIG. 8 shows a high-level block diagram of a computer that may be used to implement one or more embodiments.

A high-level block diagram of an example computer 802 that may be used to implement systems, apparatus, and methods described herein is depicted in FIG. 8. Computer 802 includes a processor 804 operatively coupled to a data storage device 812 and a memory 810. Processor 804 controls the overall operation of computer 802 by executing computer program instructions that define such operations. The computer program instructions may be stored in data storage device 812, or other computer readable medium, and loaded into memory 810 when execution of the computer program instructions is desired. Thus, the method and workflow steps or functions of FIGS. 1-5 can be defined by the computer program instructions stored in memory 810 and/or data storage device 812 and controlled by processor 804 executing the computer program instructions. For example, the computer program instructions can be implemented as computer executable code programmed by one skilled in the art to perform the method and workflow steps or functions of FIGS. 1-5. Accordingly, by executing the computer program instructions, the processor 804 executes the method and workflow steps or functions of FIGS. 1-5. Computer 802 may also include one or more network interfaces 806 for communicating with other devices via a network. Computer 802 may also include one or more input/output devices 808 that enable user interaction with computer 802 (e.g., display, keyboard, mouse, speakers, buttons, etc.).

Processor 804 may include both general and special purpose microprocessors, and may be the sole processor or one of multiple processors of computer 802. Processor 804 may include one or more central processing units (CPUs), for example. Processor 804, data storage device 812, and/or memory 810 may include, be supplemented by, or incorporated in, one or more application-specific integrated circuits (ASICs) and/or one or more field programmable gate arrays (FPGAs).

Data storage device 812 and memory 810 each include a tangible non-transitory computer readable storage medium. Data storage device 812, and memory 810, may each include high-speed random access memory, such as dynamic random access memory (DRAM), static random access memory (SRAM), double data rate synchronous dynamic random access memory (DDR RAM), or other random access solid state memory devices, and may include non-volatile memory, such as one or more magnetic disk storage devices such as internal hard disks and removable disks, magneto-optical disk storage devices, optical disk storage devices, flash memory devices, semiconductor memory devices, such as erasable programmable read-only memory (EPROM), electrically erasable programmable read-only memory (EEPROM), compact disc read-only memory (CD-ROM), digital versatile disc read-only memory (DVD-ROM) disks, or other non-volatile solid state storage devices.

Input/output devices 808 may include peripherals, such as a printer, scanner, display screen, etc. For example, input/output devices 808 may include a display device such as a cathode ray tube (CRT) or liquid crystal display (LCD) monitor for displaying information to the user, a keyboard, and a pointing device such as a mouse or a trackball by which the user can provide input to computer 802.

An image acquisition device 814 can be connected to the computer 802 to input image data (e.g., medical images) to the computer 802. It is possible to implement the image acquisition device 814 and the computer 802 as one device. It is also possible that the image acquisition device 814 and the computer 802 communicate wirelessly through a network. In a possible embodiment, the computer 802 can be located remotely with respect to the image acquisition device 814.

Any or all of the systems and apparatus discussed herein may be implemented using one or more computers such as computer 802.

One skilled in the art will recognize that an implementation of an actual computer or computer system may have other structures and may contain other components as well, and that FIG. 8 is a high level representation of some of the components of such a computer for illustrative purposes.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The invention claimed is:

1. A computer-implemented method comprising:
   receiving a plurality of input medical images comprising a first input medical image and one or more additional input medical images, the first input medical image identifying a location of a point of interest;
   extracting a set of features from each of the plurality of input medical images;
   relating features between each of the sets of features using a machine learning based relational network;
   identifying, in each of the one or more additional input medical images, a location of the point of interest that corresponds to the location of the point of interest in the first input medical image based on the related features; and
   outputting the location of the point of interest in each of the one or more additional input medical images.

2. The computer-implemented method of claim 1, wherein identifying, in each of the one or more additional input medical images, a location of the point of interest that corresponds to the location of the point of interest in the first input medical image based on the related features comprises:
   generating a heatmap identifying the location of the point of interest for each of the one or more additional input medical images based on the related features using a convolutional neural network.

3. The computer-implemented method of claim 1, wherein identifying, in each of the one or more additional input medical images, a location of the point of interest that corresponds to the location of the point of interest in the first input medical image based on the related features comprises:
   determining coordinates identifying the location of the point of interest in each of the one or more additional input medical images using a multi-layer perceptron.

4. The computer-implemented method of claim 1, wherein identifying, in each of the one or more additional input medical images, a location of the point of interest that corresponds to the location of the point of interest in the first input medical image based on the related features comprises:
   determining an assignment matrix identifying the location of the point of interest in each of the one or more additional input medical images using an optimal matching layer.

5. The computer-implemented method of claim 1, further comprising:
   decoding one or more of the sets of features extracted from the plurality of input medical images to generate an additional output.

6. The computer-implemented method of claim 1, further comprising receiving x-ray geometry information used for acquiring the plurality of input medical images, wherein extracting a set of features from each of the plurality of input medical images comprises:
   extracting the set of features from each of the plurality of input medical images and the x-ray geometry information.

7. The computer-implemented method of claim 1, further comprising:
   automatically determining the location of the point of interest in the first input medical image using a machine learning based network; and
   receiving the location of the point of interest in the first input medical image from the machine learning based network.

8. The computer-implemented method of claim 1, further comprising:
receiving user input from a user identifying the location of the point of interest in the first input medical image.

9. The computer-implemented method of claim 1, wherein the point of interest comprises an anatomical landmark or an abnormality.

10. An apparatus comprising:
means for receiving a plurality of input medical images comprising a first input medical image and one or more additional input medical images, the first input medical image identifying a location of a point of interest;
means for extracting a set of features from each of the plurality of input medical images;
means for relating features between each of the sets of features using a machine learning based relational network;
means for identifying, in each of the one or more additional input medical images, a location of the point of interest that corresponds to the location of the point of interest in the first input medical image based on the related features; and
means for outputting the location of the point of interest in each of the one or more additional input medical images.

11. The apparatus of claim 10, wherein the means for identifying, in each of the one or more additional input medical images, a location of the point of interest that corresponds to the location of the point of interest in the first input medical image based on the related features comprises:
means for generating a heatmap identifying the location of the point of interest for each of the one or more additional input medical images based on the related features using a convolutional neural network.

12. The apparatus of claim 10, wherein the means for identifying, in each of the one or more additional input medical images, a location of the point of interest that corresponds to the location of the point of interest in the first input medical image based on the related features comprises:
means for determining coordinates identifying the location of the point of interest in each of the one or more additional input medical images using a multi-layer perceptron.

13. The apparatus of claim 10, wherein the means for identifying, in each of the one or more additional input medical images, a location of the point of interest that corresponds to the location of the point of interest in the first input medical image based on the related features comprises:
means for determining an assignment matrix identifying the location of the point of interest in each of the one or more additional input medical images using an optimal matching layer.

14. The apparatus of claim 10, further comprising:
means for decoding one or more of the sets of features extracted from the plurality of input medical images to generate an additional output.

15. A non-transitory computer readable medium storing computer program instructions, the computer program instructions when executed by a processor cause the processor to perform operations comprising:
receiving a plurality of input medical images comprising a first input medical image and one or more additional input medical images, the first input medical image identifying a location of a point of interest;
extracting a set of features from each of the plurality of input medical images;
relating features between each of the sets of features using a machine learning based relational network;
identifying, in each of the one or more additional input medical images, a location of the point of interest that corresponds to the location of the point of interest in the first input medical image based on the related features; and
outputting the location of the point of interest in each of the one or more additional input medical images.

16. The non-transitory computer readable medium of claim 15, wherein identifying, in each of the one or more additional input medical images, a location of the point of interest that corresponds to the location of the point of interest in the first input medical image based on the related features comprises:
generating a heatmap identifying the location of the point of interest for each of the one or more additional input medical images based on the related features using a convolutional neural network.

17. The non-transitory computer readable medium of claim 15, the operations further comprising receiving x-ray geometry information used for acquiring the plurality of input medical images, wherein extracting a set of features from each of the plurality of input medical images comprises:
extracting the set of features from each of the plurality of input medical images and the x-ray geometry information.

18. The non-transitory computer readable medium of claim 15, the operations further comprising:
automatically determining the location of the point of interest in the first input medical image using a machine learning based network; and
receiving the location of the point of interest in the first input medical image from the machine learning based network.

19. The non-transitory computer readable medium of claim 15, the operations further comprising:
receiving user input from a user identifying the location of the point of interest in the first input medical image.

20. The non-transitory computer readable medium of claim 15, wherein the point of interest comprises an anatomical landmark or an abnormality.

* * * * *